United States Patent [19]

Petersen

[11] Patent Number: 4,773,407
[45] Date of Patent: Sep. 27, 1988

[54] METHOD AND INSTRUMENTS FOR RESECTION OF THE DISTAL FEMUR

[76] Inventor: Thomas Petersen, 5555 Reservoir Dr., San Diego, Calif. 92120

[21] Appl. No.: 888,525

[22] Filed: Jul. 23, 1986

[51] Int. Cl.⁴ ............................................. A61F 5/04
[52] U.S. Cl. ........................ 128/92 VW; 128/92 VY; 128/92 V; 128/92 R
[58] Field of Search ......... 128/92 VW, 92 VY, 92 V, 128/92 R

[56] References Cited

U.S. PATENT DOCUMENTS

| | | | |
|---|---|---|---|
| 4,457,307 | 7/1984 | Stillwell | 128/92 VW |
| 4,487,203 | 12/1984 | Androphy | 128/92 VW |
| 4,524,766 | 6/1985 | Petersen | 128/92 VW |
| 4,567,885 | 2/1986 | Androphy | 128/92 VW |
| 4,646,429 | 3/1987 | Kenna et al. | 128/92 VW |

Primary Examiner—Stephen C. Pellegrino
Assistant Examiner—Colleen M. Reilly
Attorney, Agent, or Firm—Sherman and Shalloway

[57] ABSTRACT

The present invention relates to a method and instruments for resection of the distal femur. The instruments include a distal femoral resector and a femoral alignment guide/rod. The distal femoral resector is designed to be attached to the distal femur on a plane filed on the anterior femoral cortex. The distal femoral resector includes a feeler gauge laterally adjustable to adapt to the intercondylar notch of the particular patient and further includes a rotating rod having openings therethrough for fastening pins, which rotating rod is designed to facilitate the placement of the resector on the anterior femoral cortex in a flush manner. The femoral alignment guide/rod includes a plate insertable within a slot in the resector designed for the insertion of the cutting tool and further includes a pivotable rod which may be utilized to align the resector with the mechanical axis of the leg. The rod may then be pivoted to a position facilitating the insertion of a fastening pin through the resector. The method of operating using these instruments is also disclosed.

14 Claims, 2 Drawing Sheets

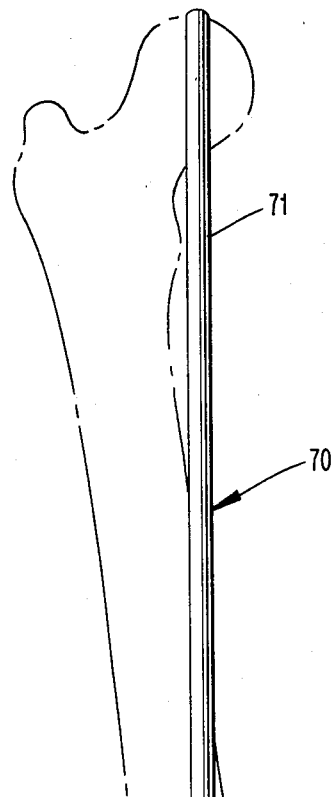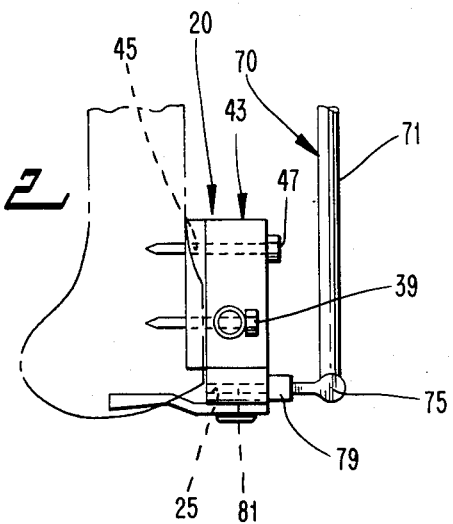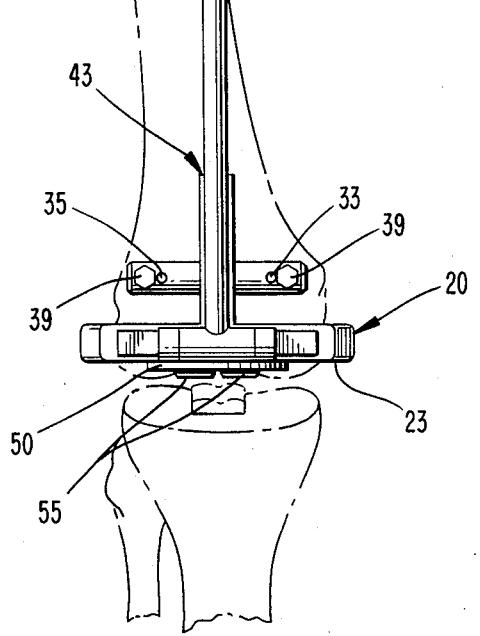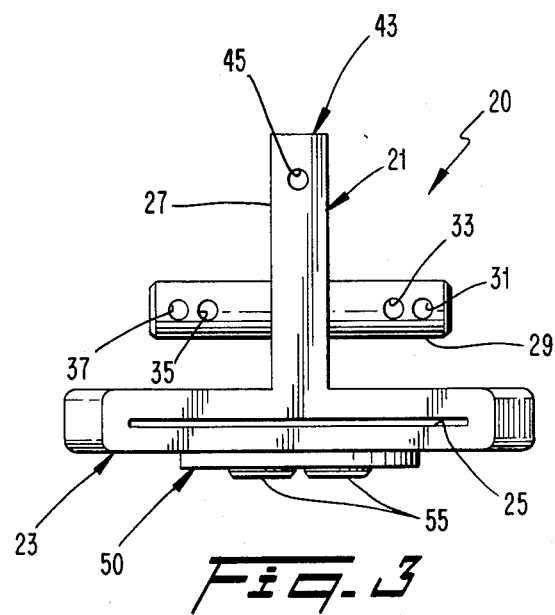

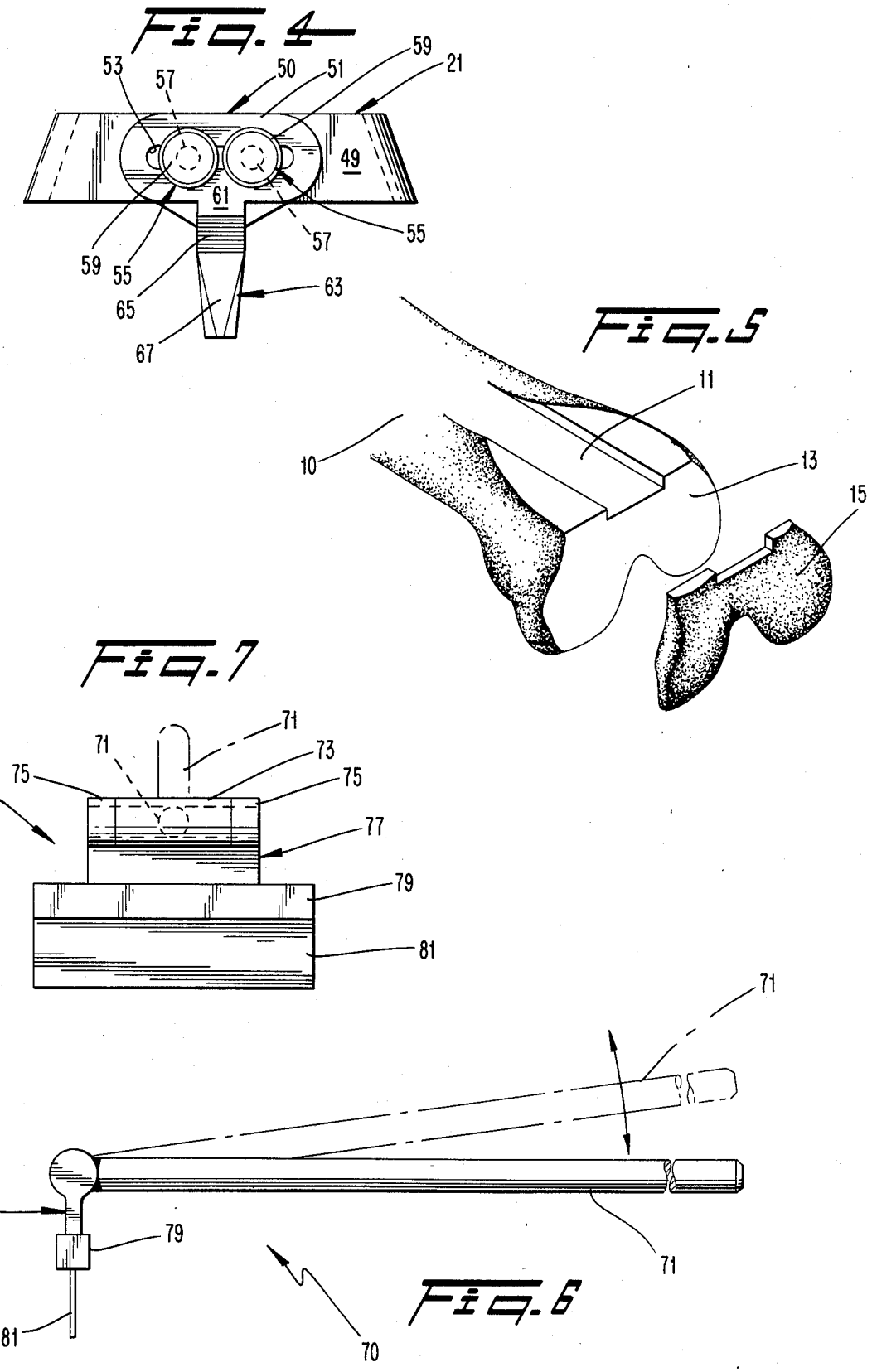

METHOD AND INSTRUMENTS FOR RESECTION OF THE DISTAL FEMUR

BACKGROUND OF THE INVENTION

The present invention relates to a method and instruments for resection of the distal femur. In the prior art, instruments are known which are utilized in resecting the distal femur so as to facilitate the installation of a distal femoral prosthesis. In general, the instruments known in the prior art are deficient because they do not enable the determination of the exact location of resection with sufficient accuracy so as to facilitate completely accurate installation of the prosthesis and proper operation of the prosthesis thereafter. The prior art includes the use of flexible cords in measuring and determining resection angles and such devices are inherently faulty as being required to be maintained in a stretched orientation at all times to maintain accuracy. Furthermore, the prior art teaches the use of alignment rods. However, no alignment rod is known to Applicant which includes the feature of being pivotably attached to a plate insertable into a slot which is intended for use as a guide with the resection tool. Thus, the interaction between the slot and the plate as well as the rod pivotably attached to the plate so as to ensure accurate resection of the distal femur perpendicular to the mechanical axis of the leg is nowhere taught in the prior art.

The following prior art is known to Applicant:

U.S. Pat. No. 4,179,810 to Kirsch discloses a device for milling slots in a jawbone for mounting an endossal device. The milling device includes a circular sawblade in a two-part housing with one part carrying the blade and the other forming a guide. Of course, guide slots for the resection of bones are well known in the art, and the present invention has significant advantages over the teacings of Kirsch when used in the environment of the resection of the distal femur such as, for example, the interaction of the guide slot on the resector with the pivotable elongated guide rod which ensures alignment of the resection in a prescribed way with respect to the mechanical axis of the leg.

U.S. Pat. No. 4,325,373 to Slavanko, et al. discloses an apparatus for forming an osteotomy for a dental implant which includes a drill guide for forming a precise elongated slot with the drill guide having pins which fit into drilled guide holes to accurately position the guide means. Of course, it is well known in the prior art to utilize pins to fasten a guiding device onto a bone which is to be resected. The present invention teaches a combination of elements nowhere found in Slavanko, et al.

U.S. Pat. No. 4,349,018 to Chambers discloses an osteotomy apparatus for use in guiding and aligning a cutting means for bone removal from the tibia and femur during knee replacement. The apparatus utilizes T bar units connected to the femur and tibia which provide support for cutting guide members that are selectively positionable for total knee replacement or proximal tibia osteotomy. Of course, the present invention is vastly different from the teachings of Chambers as including, for example, a rotating rod on the resector which enables the placement of pins in such a way that the resector will be perfectly aligned and engaged with a filed plane on the anterior femoral cortex.

U.S. Pat. No. 4,457,307 to Stillwell discloses a bone cutting device for total knee replacement which includes a femoral attached assembly and a carriage assembly connected and pivotably adjustable with respect thereto. A saw carriage on the assembly supports a powered saw for making the necessary cuts.

The present invention is much simpler than Stillwell and is more concerned with the specifics of perfectly aligning a guide slot in the resector with the appropriate area on the distal femur. Stillwell is more concerned with a guiding device for guiding the movements of a saw in its associated carriage.

U.S. Pat. No. 4,487,203 to Androphy discloses a triplanar knee resection method utilizing a single guide member selectively positionable on guide rods for performing all the necessary cuts to the distal femur or proximal tibia. The present invention is much simpler than Androphy and does not include means for performing cuts on the proximal tibia. Rather, the present invention relates to an invention which is designed for a very specific purpose, namely, the resection of the distal femur and is specifically designed so as to achieve distal femoral resection with the greatest possible accuracy.

U.S. Pat. No. 4,502,483 to Lacey discloses a method and apparatus for shaping a distal femoral surface which employs an alignment guide comprising a main body, a pivotable resection guide instrument holder, a locator pin and a femoral surface modifying instrument. A clamp is provided for affixing the main body to the femur and the locator pin is used to align the axis of the main body with the axis of the femur. While this device is generally related to the present invention, the present invention is believed to clearly distinguish therefrom since in the present invention the resector may be aligned with the mechanical axis of the body through the use of a guide/rod which is pivotable to a position wherein it may be aligned with the mechanical axis of the leg and having attached thereto a plate which may be inserted into the precise slot in the resector through which the cutting device will be inserted for the purpose of resecting the distal femur.

Further, U.S. design Pat. Nos. 272,854 to Witte, et al. and 274,162 to Kenna are also known to applicant and are believed to be only of general interest concerning the teachings of the present invention.

SUMMARY OF THE INVENTION

The present invention overcomes the deficiencies, problems and complexities of the prior art as described hereinabove and provides a new system of instruments which may be used to precisely and easily resect the distal femur during the performance of surgery to install a prosthesis on the distal femur and proximal tibia of a leg.

The present invention includes the following aspects:

(a) The method which is practiced in the present invention requires the use and interaction of two instruments. The first instrument consists of a distal femoral resector. The resector includes a housing having a guide slot extending completely therethrough at a distal portion thereof which guide slot has a dual purpose, firstly, to accomodate a plate of the second instrument for alignment purposes as will be described in greater detail hereinafter, and, secondly, to accomodate a cutting instrument which may be extended therethrough so as to enable the resection of the distal femur.

(b) The resector includes a flat bottom surface which is designed to be placed, matingly, on a filed surface formed on the anterior femoral cortex.

(c) The resector housing is of generally T-shaped configuration with the above-described guide slot being contained in the top of the "T" and with the leg of the "T" being placed upon the filed surface of the anterior femoral cortex. Extending substantially perpendicular through the leg of the "T", is a rotating rod which is rotatable to a predetermined extent with respect to the resector housing and which includes a plurality of holes therethrough which are provided so that mounting pins may be extended through the holes and then driven into the distal femur to mount the resector housing thereon. The rotating rod is rotatably mounted with respect to the resector housing so as to enable slight misalignments in the housing with respect to the filed surface to be corrected upon mounting so that the resector housing may be substantially perfectly placed in a flush manner on the filed surface of the anterior femoral cortex.

(d) The resector housing includes at least one hole therethrough at its most proximal end which hole is designed to receive therethrough an additional mounting pin which interacts with the mounting pins on the rotating rod so as to ensure the firm mounting of the resector housing on the filed surface of the anterior femoral cortex.

(e) At the most distal end of the resector housing on the distal side of the top of the "T", a sliding intercondylar notch pin is mounted through the provision of a plurality of pins extending through a laterally elongated slot in the notch pin and frictionally retained within the resector housing in the top of the "T". The sliding intercondylar notch pin may be slid laterally while the resector housing is being placed on the filed surface of the interior femoral cortex until such time as it seats within the intercondylar notch. The notch pin is provided so as to aid in stabilizing the resector housing on the filed surface of the anterior femoral cortex when the resector housing is being installed thereon for the purpose of distal femoral resection.

(f) As noted above, the second instrument which is utilized in the performance of the method of the present invention consists of a femoral alignment guide/rod. In a first aspect, the guide/rod consists of an elongated guiding element having at its distal end a hinge structure to which is pivotably mounted a depending rod alignment device which includes a hinge portion cooperating with the hinge structure of the guiding element and a depending plate which is specifically sized and configured so that it may enter the guide slot of the resector housing in the precise position and orientation with which the cutting device would so enter the guide slot. With the plate so entering the guide slot, the guiding element may be pivoted so that its proximal end is adjacent the proximal femur so as to determine whether the guiding slot is aligned in the appropriate orientation with respect to the mechanical axis of the leg.

(g) With such proper alignment being assured through this procedure, the guiding element may then be pivoted distally until it no longer overlies the proximal end of the resector housing whereupon the further mounting pin may be driven into the proximal end of the resector housing to firmly fixate the resector housing in place on the filed surface of the anterior femoral cortex so as to facilitate the accurate resection of the distal end thereof.

(h) The above-described instruments are utilized in a method of operating on the knee joint and the method will be described in detail hereinafter.

Accordingly, it is a first object of the present invention to provide method and instruments for resection of the distal femur.

It is a further object of the present invention to accomplish the method through the use of a distal femoral resector and a femoral alignment guide/rod.

It is a still further object of the present invention to provide such a distal femoral resector with a guide slot and pin mounting means which ensures secure and accurate alignment of the resector housing on a filed surface of the anterior femoral cortex.

It is a further object of the present invention to provide the femoral alignment guide/rod with a depending plate designed to interact with the guide slot in the resector housing so as to ensure the accurate alignment of the resector housing on the distal femur.

These and other objects, aspects, and features of the present invention will be better understood from the following detailed description of the preferred embodiments when read in conjunction with the appended drawing figures.

BRIEF DESCRIPTION OF THE DRAWINGS

FIG. 1 shows a frontal view of the inventive resector and guide/rod as mounted on the distal femur.

FIG. 2 shows a saggital view of the resector and guide/rod as installed on the distal femur.

FIG. 3 shows a top view of the resector.

FIG. 4 shows a front view of the sliding intercondylar notch pin of the resector.

FIG. 5 shows a perspective view of the distal femur showing the filed plane on the anterior femoral cortex thereof which receives the inventive resector.

FIG. 6 is a side view of the femoral alignment guide/rod.

FIG. 7 is a front view of the femoral alignment guide/rod.

SPECIFIC DESCRIPTION OF THE PREFERRED EMBODIMENTS

Reference is first made to FIG. 5 which shows in perspective view the distal portion of a femur 10. As shown, the distal femur has been filed on the anterior femoral cortex thereof to form a flat plane 11 on which is to be mounted the distal femoral resector. Also seen in figure 5 is a distal surface 13 of the femur 10 which is created by slicing off the distal end 15 of the femur 10. It should be understood that the distal end 15 of the femur 10 is sliced off the femur during the performance of the methods disclosed hereinafter which are accomplished through the use of the distal femoral resector and femoral alignment guide/rod which are disclosed herein.

With particular reference, now, to FIGS. 1-4, it is seen that the distal femoral resector 20 includes a T-shaped housing 21 with the top 23 of the "T" having formed therethrough a slot 25 for a purpose to be described in greater detail hereinafter.

The leg 27 of the "T" has extending therethrough in a direction substantially parallel to the direction of elongation of the top of the "T", a rotating rod 29 having a plurality of pin receiving holes 31, 33, 35 and 37 extending therethrough. In the preferred embodiment, the rotating rod 29 may rotate with respect to the leg 27 of the "T" an angular distance of approximately 30° to either side of a position of the holes 31, 33, 35 and 37 wherein they are parallel to the direction of penetration of the slot 25 into the top of the "T" 23.

As may be seen in FIGS. 1 and 2, some or all of the holes in the rotating rod 29 may have extending therethrough pins 39 which pin the rotating rod 29 and thereby the housing 21 to the distal femur.

The rotating rod 29 is rotatable as a safety feature so as to make sure that the surface 11 which has been filed on the anterior femoral cortex is engaged in a flush manner by the bottom surface 41 of the leg of the "T". As seen in FIGS. 2 and 3, at the proximal end 43 of the leg 27 of the "T", a further opening 45 is formed through which is adapted to be inserted a further pin 47 to further fixate the housing 21 on the distal femur.

With reference now to FIGS. 2, 3 and 4, it is seen that mounted at the distal end of the housing 21 on a distal wall 49 of the top of the "T", is a sliding intercondylar notch pin 50. As may be seen in FIG. 4, the notch pin 50 includes a T-shaped configuration with the top of the "T" 51 having a laterally elongated slot 53 through which are inserted two pins 55. Two pins 55 are used so as to constrain the lateral movements of the notch pin 50 to linear movements along the lateral extent of the elongated slot 53. The pins 55 have stems 57 which are frictionally retained within openings (not shown) in the distal wall 49 of the top of the "T" 32 of the housing 21 of the resector 20. The length of the stems 57 is chosen so that the undersides of the heads 59 of the pins 55 will frictionally engage the distal surface 61 of the top of the "T" 51 of the notch pin 50 so that slight pressure is necessary to laterally move the notch pin 50, however, the frictional forces are quite slight and movements of the resector 20 on the anterior femoral cortex will provide sufficient force application to the notch pin 50 to enable it to slide with respect to the fixed pins 55 to thereby enable its adjustment with respect to the intercondylar notch of the distal femur.

Depending downwardly from the top of the "T" 51, of the notch pin 51, is a pin member 63 which includes an angled portion 65 slightly angling in the proximal direction and a vertically depending portion 67 which is designed to fit into the intercondylar notch.

With reference now to FIGS. 1, 2, 6 and 7, it is seen that the femoral alignment guide/rod 70 includes a proximal rod 71 comprising a guiding element having connected at its distal end a hinge 73, 75 with the hinge portion 73 being integrally attached to the rod 71 and with the hinge portion 75 being attached to a rod aligning portion 77 thereof consisting of a rectangular cubic portion 79 having depending therefrom an elongated flat plate 81 sized and configured to fit precisely within the slot 25 of the resector housing 21. As should be understood, the pivoting motion of the rod 71 is constrained in a direction perpendicular to the direction of lateral elongatin of the plate 81. Thus, when the plate 81 is inserted within the slot 25 of the resector housing 21, the pivoting of the rod 71 should be in a plane parallel to the direction of elongation of the leg 27 of the resector housing 21. Thus, with the plate 81 inserted into the slot 25 of the resector housing 21, the rod 71 may be pivoted to the position shown in FIG. 1 so that the alignment of the resector housing 21 as compared to the mechanical axis of the leg may be determined.

Thus, with the plate 81 inserted within the slot 25 of the resector housing 21, the directin of elongation of the rod 71 in the position shown in FIG. 1 may be compared with the mechanical axis of the leg and if there is misalignment, the resector housing 21 may be rotated or otherwise moved so as to ensure precise alignment of the rod 71 with the mechanical axis of the leg. When the rod 71 is aligned with the mechanical axis of the leg, the resector housing 21 will then be in perfect alignment at least laterally for the impending resection. Then, with such alignment existing, the resector housing 21 may be moved distally or proximally as may be the case so as to ensure lateral movements of the notch pin 50 until such time as the notch pin 50 properly seats in the intercondylar notch and the housing 21 is then perfectly aligned for the impending resection. At this point, pins such as those that are designated by the reference numeral 39 in FIGS. 1 and 2 may be driven through the rotating rod 29 with the resector housing 21 being adjusted through rotation of the rotating rod 29 with respect thereto so as to ensure that the bottom surface 41 of the leg 27 thereof is perfectly flush on the filed surface of the anterior femoral cortex designated by the reference numeral 11 in FIG. 5.

At this point, the rod 71 may be pivoted upwardly away from the femur so as to expose to the surgeon the opening 45 through the proximal end of the leg 27 of the resector housing 21. Thereafter, the pin 47 may be driven through the opening 45 and into the distal femur so as to securely fix the resector housing 21 thereon at at least three points, through the use of the pins 39 and 47.

Now, with the distal femoral resector 20 and the femoral alignment guide/rod 70 having been described in detail and with the methods of use being at least inferentially described, the methods of use will now be described in terms of their preferred mode of operation. The following steps comprise the preferred method of operation of the inventive instruments 20 and 70:

(a) As seen in FIG. 5, the distal femur is prepared for the attachment of the resector 20 through the filing of the anterior femoral cortex to form the surface 11.

(b) Thereafer, the resector 20 is placed on the filed surface 11 of the anterior femoral cortex in the positin best seen in FIG. 1.

(c) Thereafter, the plate 81 of the femoral alignment guide/rod 70 is inserted into the slot 25 in the resector housing 21 and the rod 71 of the guide/rot 70 is pivoted to the position shown in FIGS. 1 and 2.

(d) The direction of elongatin of the rod 71 is then compared with the mechanical axis of the leg and the rod 71 is moved with the resector housing 21 moving along therewith until such time as the rod 71 is aligned with the mechanical axis of the leg.

(e) Thereafter, with the rod 71 being maintained in alignment with the mechanical axis of the leg, the housing 21 is further moved proximally or distally until such time as the sliding intercondylar notch pin 50 is properly seated within the intercondylar notch of the distal femur.

(f) With the above steps having been accomplished, pins are driven into the rotating rod 29 as shown in FIG. 1 to at least partially fixate the position of the resector housing 21 with respect to the distal femur. With the pins 39 having been driven in through the openings in the rotating rod 29, the rotation of the rotating rod 29 with respect to the resector housing 21 will allow the bottom surface 41 thereof to be adjusted in its orientation so that it lies completely flush against the surface 11 which has been filed in the anterior femoral cortex of the distal femur.

(g) With this having been accomplished, the rod 71 may be pivoted upwardly away from the resector housing 21 to expose the opening 45 in the proximal end of the leg 27 of the resector housing 21. With the rod 71 having been so pivoted, a further pin 47 (FIG. 2) may be driven through the opening 45 and into the femur to thereby fix the position of the resector housing 21 on the distal femur at at least 3 points.

(h) With the pin having been driven through the opening 45, the femoral alignment guide/rod 70 may be removed from the resector housing 21 by lifting the plate 81 thereof from the slot 25 of the resector 20.

(i) Thereafter, a cutting instrument may be inserted through the slot 26 of the resector 20 and may be operated in a manner well known to those skilled in the art to slice off the distal end 15 (FIG. 5) of the femur.

(j) Thereafter, the additional procedures which are necessary to install a distal femoral prosthesis are carried out. These procedures do not form a part of the present invention.

Accordingly, an invention has been disclosed in terms of a method of operating and the instruments used to perform the method. Of course, various modifications alterations and changes in the methods and instruments may be contemplated by those skilled in the art without departing from the intended spirit and scope of the present invention. Accordingly, it is intended that the present invention only be limited by the terms of the appended claims.

I claim:

1. A distal femoral resector for use in resecting the distal femur of a leg, said distal femur having a substantially flat surface formed on the anterior femoral cortex thereof, said resector comprising:
   (a) a base of substantially T-shaped configuration and adapted to be placed in overlying relation to said substantially flat surface, siad substantially T-shaped configuration being defined by a proximal leg portion and a distal transverse portion;
   (b) an intercondylar notch pin attached to a distal side of said transverse portion; and
   (c) a rotating rod rotatably mounted through said leg portion and including means for attaching said base to said distal femur, said rod being rotatable to facilitate firm and flush attachment of said base to said substantially flat surface.

2. The invention of claim 1, wherein said notch pin is laterally slidable with respect to said transverse portion so as to enable said base to be adaptable to intercondylar notches of differing configurations.

3. The invention of claim 1, wherein said means for attaching comprises a plurality of passages extending therethrough and a pin extending through at least some of said passages and driven into said distal femur.

4. The invention of claim 1 wherein said distal transverse portion includes an elongated slot extending therethrough and adapted to receive therethrough means for resecting said distal femur, said slot being operative to guide said means for resecting.

5. The invention of claim 1, wherein said proximal leg portion includes further means for attaching said base to said distal femur.

6. The invention of claim 5, wherein said further means for attaching comprises a passage through a proximal end of said proximal leg portion and a pin extending through said passage and into said distal femur.

7. The invention of claim 4, wherein said elongated slot is also adapted to receive therethrough a plate incorporated into means for aligning said resector.

8. The invention of claim 7, wherein said means for aligning comprises:
   (a) a base member;
   (b) said plate depending from said base member;
   (c) a guide rod pivotably mounted to said base member and pivotable, when said plate is within said elongated slot, from a position overlying said proximal leg portion to a position remote therefrom.

9. The invention of claim 8, wherein said base member and guide rod are pivotably connected through a hinge, and whereby in said overlying position of said guide rod, the orientation of said base with respect to the mechanical axis of said leg may be adjusted.

10. The invention of claim 9, wherein said proximal leg portion includes further means for attaching said base to said distal femur, and after said orientation of said base is adjusted, said guide rod may be pivoted to said remote position to thereby expose said further means for attaching.

11. A method of resecting the distal femur of a leg, including the steps of:
    (a) filing a surface on the anterior femoral cortex;
    (b) placing the base of a distal femoral resector on said surface;
    (c) said resector including a guide slot extending therethrough for guiding a cutting tool in resecting said distal femur;
    (d) providing an alignment device;
    (e) using said alignment device to align said resector with the mechanical axis of said leg;
    (f) firmly fixing said base to said surface; and
    (g) resecting said distal femur.

12. The method of claim 11, wherein said resector further includes an adjustable intercondylar notch pin, and said placing step including the step of aligning said notch pin with the intercondylar notch of said femur.

13. The method of claim 11, wherein said alignment device includes a guide plate and a guide rod pivotably mounted thereto, and further wherein said using step includes the steps of:
    (a) inserting said guide plate into said guide slot;
    (b) pivoting said guide rod to a first position wherein said resector may be aligned with the mechanical axis of said leg;
    (c) performing said alignment of said resector with the mechanical axis of said leg;
    (d) pivoting said guide rod to a second position prior to said firmly fixing step;
    (e) removing said guide plate from said guide slot prior to said resecting step.

14. The method of claim 11, wherein said base includes a rotating rod including means thereon for fixing said base to said surface, and said placing step further including the step of intially fixing said rotating rod to said surface with the rotating rod being rotatable to align said base to said surface, said firmly fixing step including the step of fixing said base to said surface with fixation means extending through said base.

* * * * *